(12) United States Patent
Abromeit

(10) Patent No.: US 7,771,923 B2
(45) Date of Patent: Aug. 10, 2010

(54) **METHOD FOR DETECTING THE VIABILITY OF *TRICHURIS SUIS* EGGS**

(75) Inventor: Norbert Abromeit, Ahrensburg (DE)

(73) Assignee: Ovamed GmbH, Barsbuttel (DE)

( * ) Notice: Subject to any disclaimer, the term of this patent is extended or adjusted under 35 U.S.C. 154(b) by 511 days.

(21) Appl. No.: 11/750,534

(22) Filed: May 18, 2007

(65) Prior Publication Data

US 2007/0269795 A1   Nov. 22, 2007

(30) Foreign Application Priority Data

May 19, 2006   (DE) ........................ 10 2006 023 906

(51) Int. Cl.
*C12Q 1/00* (2006.01)
(52) U.S. Cl. ........................................................ 435/4
(58) Field of Classification Search ........................ None
See application file for complete search history.

(56) References Cited

OTHER PUBLICATIONS

Huffman J. L. and Jones A. W. Hatchability, viability, and infectivity of Hydatigera taeniaeformis eggs, Experimental Parasitology, 1962, vol. 12, issue 2, pp. 120-124.*
Panesar T. S and Croll N. A. The hatching process in Trichuris muris (nematoda: trichuroidea), Can. J. Zool., 1981, vol. 59 (4): 521-628.*
Burden D.J. and Hammet N.C. A comparision of the infectivity of Trichuris suis ova embryonated by four different methods, Veterinary Parasitology, Nov. 1976, vol. 2, issue 3, pp. 307-311.*
Lackie A. M. The activation of infective stages of endoparasites of vertebrates, Biological Reviews (Cambridge philosophical Society, London), Aug. 1975, vol. 50, issue 3, pp. 285-323.*
Medhekar R. The first quantitative evidence providing the efficacy of supplemental enzymes, National Enzyme Company, 2004, an online research report, pp. 1-7.*
Gaspard P. et al. A method for assessing the viability of nematode eggs in sludge, Environmental Technology, Apr. 1996, vol. 17(4), pp. 415-420.*
Jaskoski B. J. and Colucci A. V. In vitro hatching of *Ascaris suum* eggs, Transactions of the American microscopical Society, Jul. 1964, vol. 83(3), pp. 294-300.*
Black, et al; "Survival Rates of Parasite Eggs in Sludge During Aerobic and Anaerobic Digestion": Applied and Environmental Microbiology, vol. 44, No. 3, Nov. 1992, pp. 1138-1143.

* cited by examiner

*Primary Examiner*—Jon P Weber
*Assistant Examiner*—Satyendra K Singh
(74) *Attorney, Agent, or Firm*—Norris McLaughlin & Marcus, P.A.

(57) ABSTRACT

A method for detecting the viability of *Trichuris suis* eggs by simulating in vitro a passage of the eggs through the gastrointestinal passage of a swine with regard to chronological sequence and medium. The method involves subjecting the eggs in vitro first to gastric simulation in gastric medium and then to intestinal simulation in intestinal medium in decreasing enzyme and salt concentrations and thereby inducing the larvae to shed from the eggs. The shedding of larvae from the eggs indicates that the eggs are viable.

15 Claims, No Drawings

METHOD FOR DETECTING THE VIABILITY OF *TRICHURIS SUIS* EGGS

The present invention relates to a method for detecting the viability of *Trichuris suis* eggs.

*Trichuris suis* (swine whipworm) belongs to the group of roundworms (nematodes) that live as parasites in the swine intestine, and it is of particular interest pharmacologically for treatment of excessive immune reactions as described in WO 99/33479, where production of *Trichuris suis* eggs is described as well as the inoculation and treatment of the intestine of human patients who have advanced medication-resistant Crohn's disease with *Trichuris suis*.

For such use as well as other uses, it is of interest to know the viability of the *Trichuris suis* eggs being used. In the past this has been done by infesting swine free of *Trichuris suis* with *Trichuris suis* eggs, the active pharmaceutical ingredient, then slaughtering the swine treated in this way and examining the intestine for *Trichuris suis*.

One disadvantage of this procedure is the great expense with regard to swine free of *Trichuris suis*, raising them and accommodating them and then slaughtering them. Another disadvantage is the long duration of such a test for *Trichuris suis* eggs, which must be tested for viability in this way.

An object of the present invention was to remedy this situation and in particular to create a method for detecting the viability of *Trichuris suis* eggs that will not have the disadvantages of the state of the art or at least will not have them to the current extent, wherein the method can be performed in vitro in particular, is economical, standardized and can be performed by trained personnel.

This and other objects were met by the present invention, which, as noted above, relates generally to a method for detecting the viability of *Trichuris suis* eggs as described herein. In one embodiment, the inventive method is characterized in that the passage of the eggs through the gastrointestinal passage of a swine is simulated in vitro with regard to the chronological sequence and medium, namely the gastric medium first, and then the intestinal medium and therefore the larvae from the eggs are shed in decreasing enzyme concentration and salt concentration.

Simulation of the gastrointestinal passage of a swine is accomplished by adding corresponding enzymes and salts and incubating at an elevated temperature, whereby the following parameters are advantageously adjusted, in particular:
- enzymes in decreasing concentration in the intestinal simulation,
- pH,
- heat,
- possibly different gas concentrations in the climate compartment,
- agitating movements,
- salt solutions in decreasing concentration in the intestinal simulation.

In this way, the first larval stage can be shed in a liquid or semisolid medium, in particular in a solution.

Essentially enzymes include all digestive substances, enzymes and enzyme mixtures that act like intestinal enzymes and in general induce degrading or modifying properties of the gastrointestinal content (gastrointestinal reactions). An enzyme concentration that declines over a period of time is an important triggering factor in shedding.

In simulation of the stomach, preferably 1-5% pepsin is used (all percentage amounts are wt %, percent by weight).

In simulation of the intestine, an initial total enzyme concentration of 0.5-12%, especially preferably 1-8%, is used (including the bile extract/salts). An initial concentration of pancreatin, trypsin and bile extract/salts of 0.3-3% each is also preferred, 0.1-0.8% for the first dilution, 0.02-0.2% for the second dilution, 0.005-0.1% for the third dilution and 0.002-0.09% for the fourth dilution. Two dilutions are advantageous, but three or four dilutions are preferred. The total enzyme concentration thus preferably declines by more than 70%, especially preferably by more than 90%.

Specific values for an advantageous intestinal simulation are given in the following table.

TABLE 1

Declining enzyme concentration in the egg solution during the intestinal simulation.

| Dilution steps | Enzyme | | |
| --- | --- | --- | --- |
| | Pancreatin | Trypsin | Bile extract/salts |
| Initial concentration | Approx. 0.9% | Approx. 0.5% | Approx. 2.0% |
| First dilution | Approx. 0.18% | Approx. 0.1% | Approx. 0.4% |
| Second dilution | Approx. 0.06% | Approx. 0.033% | Approx. 0.13% |
| Third dilution | Approx. 0.01% | Approx. 0.0055% | Approx. 0.022% |
| Fourth dilution | Approx. 0.005% | Approx. 0.0028% | Approx. 0.011% |

Just parts of the intestinal passage simulation are sufficient according to the invention to induce shedding. Likewise, according to the invention, it is sufficient to simulate only portions of the gastrointestinal passage of a swine, in particular to disregard the medium of the mouth and the esophagus. However, simulation of the mouth and/or esophagus may advantageously occur prior to the gastric simulation. Likewise, it is sufficient according to the invention to use only individual enzymes (in decreasing concentration in the gastric simulation).

With an optional simulation of the mouth preferably 1-5% amylase is used.

The following digestive substances, salts, enzymes or enzyme mixtures may be mentioned as advantageous enzyme examples; with their help larvae from the eggs can be brought to shed according to the invention:

1. Amylase from swine or other animals, in particular in a concentration between 0.1% and 10%.
2. Pepsin of swine or other animals in particular in a concentration between 0.1% and 10%, advantageously in a highly acidified PBS solution (salt buffer) (pH in particular 0.8-3).
3. Bile extract/salts of swine or other animals, in particular in a concentration between 0.5% and 12%.
4. Pancreatin of swine or other animals, in particular in a concentration between 0.1% and 10%.
5. Trypsin of swine or other animals, in particular in a concentration between 0.01% and 1%.

The enzymes and bile extract/salts of swine are especially preferred (herein "swine" is preferably understood to refer to a domestic pig). The enzymes and digestive substances are advantageously dissolved in a PBS solution (other isotonic or nonisotonic salt solutions are possible). The pH is preferably varied during the simulation of the gastrointestinal passage. The pH is in particular between 0.8 and 3.0 (in simulation of the gastric passage) and in particular between 5 and 8 (in simulation of the intestinal passage).

The eggs are advantageously incubated in a climate cabinet or a hot box at temperatures in particular between 35° C. and 43° C., especially preferably 39.4° C., whereby the gas concentration, in particular the $CO_2$ content, is advantageously adjusted, with a $CO_2$ content of 4-7%, especially preferably 5.6% (remainder air), being especially advantageous.

The egg enzyme mixture is preferably agitated on an agitator in the climate box or heat box, whereby the larvae are shed after approximately 24 to 168 hours.

The invention will now be explained in greater detail on the basis of an exemplary embodiment but without attempting to unnecessarily restrict the scope.

EXAMPLE

In vitro gastrointestinal passage simulated according to this invention, leading to shedding of the first larval stage of the swine whipworm *Trichuris suis* from the egg.

Chemical and enzyme solutions used in shedding *Trichuris suis* larvae from the eggs (all solutions were prepared fresh shortly before use):

1. PBS buffer (Dulbecco's phosphate buffered saline W/O Ca/Mg): purchased buffer ready-to-use without any change.

2. HCl solution: 1 mL of a 25% HCl solution is dissolved in 49 mL PBS buffer (1).

3. Potassium monohydrogen phosphate buffer: 1.9 g; potassium monohydrogen phosphate is dissolved in 48 mL PBS buffer (1).

4. Amylase: 0.5 g amylase is dissolved in 12.5 mL PBS buffer (1).

5. Pepsin solution: 1.25 g pepsin is dissolved in 25 mL of the HCl solution prepared in point 2.

6. Pancreatin-trypsin solution: 0.225 g pancreatin and 0.083 g trypsin are dissolved in 12.5 mL PBS buffer (1). Pancreatin and trypsin are dissolved 1.5 hours before they are used and then are mixed for one hour on a rotator at 39.4° C. Then the solution is stored for 0.5 hours in refrigeration so that large particulate matter can settle out. Solution for the experiments is taken from the top third.

7. Bile extract/salt solution: 5 g bile extract is dissolved in 25 mL PBS buffer (1). Bile extract is dissolved 1.5 hours before use and mixed for one hour on a rotator at 39.4° C. Then the solution is stored for 0.5 hours in refrigeration so that larger particulate matter can settle out. Solution for the experiments is taken from the top third.

8. Respiratory air mixture: 94.4% respiratory air plus 5.6% $CO_2$.

TABLE 2

Manufacturer and items numbers of the solutions, chemicals and enzymes used.

| | Solution/Chemical | Manufacturer | Item number |
|---|---|---|---|
| 1 | PBS buffer | Invitrogen | 14190169 |
| 2 | 25% HCl solution | Merck | 1.00316.1000 |
| 3 | Potassium monohydrogen phosphate | Synopharm | 163690-0001 |
| 4 | Amylase | Sigma-Aldrich | A3176-500KU |
| 5 | Pepsin | Sigma-Aldrich | P-7000 25 g |
| 6 | Pancreatin | Fluka | 76190 |
| 7 | Trypsin | Sigma-Aldrich | T4799-5G |
| 8 | Bile extract/salts | Sigma-Aldrich | B 8631-100G |
| 9 | Respiratory air mixture with 5.6% $CO_2$ | Linde | Special production |
| 10 | Original egg solution | Parasite Technology | Batch PT-M32 |
| 11 | Purified egg solution | Ovamed | 1602 |

TABLE 3

Laboratory equipment used.

| | Equipment | Manufacturer | Type |
|---|---|---|---|
| 1 | Centrifuge | Hettich | Rotixa 50 S |
| 2 | Laminar air flow | Holton | HB 2460 |
| 3 | Incubator | Binder | BD 53 |
| 4 | Agitator | Kinematica | VXR S13 |
| 5 | Rotator | Stuart | 5B2 |

Procedure:

Day 1

The egg solution is prepared from the original egg solution, with a pH of 7 and an egg count of approx. 500 embryonated eggs per mL. From the egg solution 20 mL (approx. 10,000 embryonated eggs) are removed and transferred to a Falcon tube.

The egg solution is centrifuged for 5 minutes at 500 rpm in the centrifuge (all other centrifugation steps are performed at this setting) so that the eggs sink to the base of the Falcon tube due to the centrifugal force.

The Falcon tube is subjected to an external disinfection and placed under the laminar air flow (LF). Under LF, 19.5 mL of the supernatant is pipetted off and discarded (solutions are added and removed only under LF, but this is not absolutely essential).

0.5 mL PBS buffer and 1 mL of the amylase solution are added to the Falcon tube.

The Falcon tube is sealed and placed on the agitator where it is incubated with slight agitating movements (between 50 and 100 rpm, no change during the experiment) at 39.4° C. for 0.5 hours in an incubator.

The solution is centrifuged. 1.5 mL supernatant is pipetted off and discarded, then 1 mL of the prepared pepsin solution and 1 mL of the prepared HCl solution are added.

The Falcon tube is sealed and incubated on the agitator for 3 hours at 39.4° C. in the incubator with light agitation movements.

6 mL of the potassium monohydrogen phosphate solution is pipetted into the tube. This results in an increase in pH.

The solution is centrifuged. 7 mL supernatant is pipetted off and discarded.

2.5 mL PBS buffer, 5 mL pancreatin-trypsin solution and 1 mL bile extract/salt solution are added to the 1.5 mL neutral solution.

Starting at this point, after opening each Falcon tube, the respiratory air mixture containing 5.6% $CO_2$ is blown into the air space of the Falcon tube over the solution. The Falcon tube is sealed and incubated for 3 hours at 39.4° C. in the incubator on the agitator.

The solution is divided between two Falcon tubes and each tube is treated further in the same way. The remaining procedure will now be described for one Falcon tube.

20 mL PBS buffer is pipetted into the Falcon tube. The Falcon tube is sealed and incubated for 16 hours at 39.4° C. in an incubator on the agitator.

Day 2

The solution is centrifuged. 20 mL supernatant is pipetted off and discarded. 10 mL PBS buffer is added.

The Falcon tube is sealed and incubated for 3 hours at 39.4° C. in the incubator on the agitator.

The solution is centrifuged. 13 mL supernatant is pipetted off and discarded. 10 mL PBS buffer is added.

The solution is centrifuged. 6 mL supernatant is pipetted off and discarded.

The Falcon tube is sealed and incubated for 3 hours at 39.4° C. in the incubator on the agitator.

6 mL PBS buffer is added.

The Falcon tube is sealed and incubated for 16 hours at 39.4° C. in the incubator on the agitator.

Day 3

The solution is centrifuged. 6 mL supernatant is pipetted off and discarded.

The Falcon tube contains approx. 6 mL dilute enzyme solution and approx. 5000 embryonated eggs. The tube is incubated for 24 hours at 39.4° C. in the incubator on the agitator.

Day 4

Inspection of the solution for shed larvae. The tube is incubated for 24 hours at 39.4° C. in the incubator with slight agitating movements.

Day 5

Inspection of the solution for shed larvae. The tube is incubated for 24 hours at 39.4° C. in the incubator on the agitator.

Day 6

Inspection of the solution for shed larvae. The tube is incubated for 24 hours at 39.4° C. in the incubator on the agitator.

Day 7

Inspection of the solution for shed larvae. The tube is incubated for 24 hours at 39.4° C. in the incubator on the agitator.

Day 8

Inspection of the solution for shed larvae. The tube is incubated for 24 hours at 39.4° C. in the incubator on the agitator.

From day 4 through 5, the number of viable larvae increases from approx. 2% to approx. 10%. After day 6, the number of living organisms drops. The rate of dead organisms increases continuously from day 3 (2-4%) to day 8 (more than 50%). It may be assumed that all the dead larvae have been actively shed and were thus alive at the time of shedding.

What is claimed is:

1. A method for detecting the viability of *Trichuris suis* eggs, said method comprising simulating in vitro a passage of the eggs through the gastrointestinal passage of a swine with regard to chronological sequence and medium by subjecting the eggs in vitro first to gastric simulation in gastric medium and then to intestinal simulation in intestinal medium in decreasing enzyme and salt concentrations and thereby inducing the larvae to shed from the eggs, whereby shedding of larvae from the eggs indicates that the eggs are viable.

2. Method according to claim 1, wherein the simulating of the gastrointestinal passage of a swine is accomplished by adding corresponding enzymes to one or more of said media and incubating at an elevated temperature, whereby the following parameters are set:
   enzymes in decreasing concentration in the intestinal simulation,
   pH,
   heat,
   optionally different gas concentrations in a climate compartment,
   agitating movements,
   salt solutions in decreasing concentration in the intestinal simulation.

3. Method according to claim 1, wherein the simulating is performed in a liquid or semisolid medium.

4. Method according to claim 3, wherein the simulating is performed in a solution.

5. Method according to claim 1, wherein the intestinal medium has an enzyme concentration that decreases over time.

6. Method according to claim 1, wherein the gastric medium and/or intestinal medium comprises digestive substances, salts, enzyme mixtures or enzymes.

7. Method according to claim 6, wherein the digestive substances, salts, enzyme mixtures or enzymes are one or more enzymes and/or salts selected from the group consisting of amylase of the swine or other animals, optionally in a concentration between 0.1% and 10%; pepsin of swine or other animals, optionally in a concentration between 0.1% and 10%, and/or optionally in a highly acidified PBS buffer solution; bile extract/salts of the swine or other animals, optionally in a concentration between 0.5% and 12%; pancreatin of the swine or other animals, optionally in a concentration between 0.1% and 10%; trypsin of the swine or other animals, optionally in a concentration between 0.01% and 1%; and enzymes and salts are used at the following pH levels:

| Enzyme | pH |
| --- | --- |
| Amylase | 5-8 |
| Pepsin | 0.3-3 |
| Pancreatin | 5-8 |
| Trypsin | 5-8 |
| Bile extract/salts | 5-8. |

8. Method according to claim 1, wherein the gastric medium and/or intestinal medium comprise enzymes of the swine.

9. Method according to claim 1, wherein the pH of the gastric medium is between 0.8 and 3.0 for simulating the gastric passage and the pH of the intestinal medium is between 5 and 8 for simulating the intestinal passage.

10. Method according to claim 1, wherein the simulating is performed at a temperature between 35° C. and 43° C.

11. Method according to claim 10, wherein the simulating is performed at 39.4° C.

12. Method according to claim 1, wherein a $CO_2$ content above the medium is adjusted to 4-7%, remainder being air.

13. Method according to claim 12, wherein the $CO_2$ content is 5.6%, remainder being air.

14. Method according to claim 1, which comprises the following treatments: first exposing the eggs to a simulated porcine gastric medium; then separating the eggs from this medium, optionally by centrifugation; next exposing the eggs treated in this way to a simulated porcine intestinal medium, wherein the enzyme concentration of this simulated porcine intestinal medium is adjusted to decrease over time, optionally by dilution, wherein these treatments are advantageously performed under an atmosphere comprising $CO_2$ where the $CO_2$ content is 4-7% at a temperature of 35-43° C.

15. Method according to claim 14, wherein the $CO_2$ content is 5.6% and/or the temperature is 39.4° C.

* * * * *